United States Patent
Rocha

(10) Patent No.: US 11,096,773 B2
(45) Date of Patent: Aug. 24, 2021

(54) IMPLANTABLE ARTIFICIAL BRONCHUS AND USE OF AN IMPLANTABLE ARTIFICIAL BRONCHUS

(71) Applicant: Murilo Pundek Rocha, São Paulo (BR)

(72) Inventor: Murilo Pundek Rocha, São Paulo (BR)

(73) Assignee: PULMAIR MEDICAL, INC., Del Mar, CA (US)

( * ) Notice: Subject to any disclaimer, the term of this patent is extended or adjusted under 35 U.S.C. 154(b) by 317 days.

(21) Appl. No.: 16/055,686

(22) Filed: Aug. 6, 2018

(65) Prior Publication Data

US 2018/0344445 A1 Dec. 6, 2018

Related U.S. Application Data

(63) Continuation of application No. 15/156,841, filed on May 17, 2016, now Pat. No. 10,806,560.

(30) Foreign Application Priority Data

May 18, 2015 (BR) .................. 10 2015 0113765

(51) Int. Cl.
*A61F 2/04* (2013.01)
*A61F 2/24* (2006.01)

(52) U.S. Cl.
CPC .............. *A61F 2/04* (2013.01); *A61F 2/2476* (2020.05); *A61F 2002/043* (2013.01);
(Continued)

(58) Field of Classification Search
CPC ...... A61F 2/04; A61F 2/24; A61F 2210/0071; A61F 2250/0069; A61F 2310/00023;
(Continued)

(56) References Cited

U.S. PATENT DOCUMENTS

| 5,269,802 A | 12/1993 | Garber |
| D380,831 S | 7/1997 | Kavteladze et al. |

(Continued)

FOREIGN PATENT DOCUMENTS

| EP | 1524942 A2 | 7/2005 |
| WO | 0187170 A1 | 11/2001 |

(Continued)

OTHER PUBLICATIONS

International Search Report and Written Opinion for International Patent Application No. PCT/US2019/062132 dated Feb. 5, 2020, 11 pages.

(Continued)

*Primary Examiner* — Jerrah Edwards
*Assistant Examiner* — Rokhaya Diop
(74) *Attorney, Agent, or Firm* — Morgan, Lewis & Bockius LLP

(57) ABSTRACT

A method of promoting lung disinsufflation including inserting a catheter into a bronchial passage of a patient's lung. The catheter contains an implantable artificial bronchus compressed within the catheter. The method further includes using the catheter to position the implantable artificial bronchus in the bronchial passage such that the implantable artificial bronchus extends across openings of a plurality of other bronchial passages and withdrawing the catheter from the bronchial passage to cause the implantable artificial bronchus to naturally expand and remain in the bronchial passage. The implantable artificial bronchus is configured to promote enlargement of the bronchial passage and allow air to exit from the plurality of other bronchial passages and into the implantable artificial bronchus through one or more of the plurality of side openings.

20 Claims, 7 Drawing Sheets

(52) U.S. Cl.
CPC .............. *A61F 2210/0071* (2013.01); *A61F 2230/0067* (2013.01); *A61F 2230/0069* (2013.01); *A61F 2250/0069* (2013.01); *A61F 2310/00023* (2013.01)

(58) Field of Classification Search
CPC ........ A61F 2002/043; A61F 2230/0067; A61F 2230/0069; A61B 17/12; A61B 17/12104; A61B 17/1214
See application file for complete search history.

(56) References Cited

U.S. PATENT DOCUMENTS

| | | | |
|---|---|---|---|
| 5,667,486 A | 9/1997 | Mikulich et al. | |
| 5,938,697 A | 8/1999 | Killion et al. | |
| 6,168,617 B1 | 1/2001 | Blaeser et al. | |
| 6,409,750 B1 | 6/2002 | Hyodoh et al. | |
| D484,979 S | 1/2004 | Fontaine | |
| 6,770,101 B2 | 8/2004 | Desmond, III et al. | |
| 6,792,979 B2 | 9/2004 | Konya et al. | |
| 7,011,094 B2 | 3/2006 | Rapacki et al. | |
| D553,746 S | 10/2007 | Fliedner | |
| 7,402,169 B2 | 7/2008 | Killion et al. | |
| D612,499 S | 3/2010 | Ondracek et al. | |
| 7,780,719 B2 | 8/2010 | Killion et al. | |
| 7,857,844 B2 | 12/2010 | Norton et al. | |
| 7,896,887 B2 | 3/2011 | Rimbaugh et al. | |
| D660,967 S | 5/2012 | Braido et al. | |
| 8,323,351 B2 | 12/2012 | Kubena et al. | |
| 8,414,635 B2 | 4/2013 | Hyodoh et al. | |
| 8,474,460 B2 | 7/2013 | Barrett et al. | |
| 8,568,488 B2 | 10/2013 | Stack et al. | |
| 8,585,628 B2 | 11/2013 | Harris et al. | |
| 8,623,067 B2 | 1/2014 | Berez et al. | |
| 8,709,080 B2 | 4/2014 | Marten et al. | |
| 8,808,360 B2 | 8/2014 | Laguna | |
| D723,166 S | 2/2015 | Igaki et al. | |
| 8,974,516 B2 | 3/2015 | Hyodoh et al. | |
| D732,666 S | 6/2015 | Nguyen et al. | |
| 9,173,736 B2 | 11/2015 | Bertini | |
| 9,265,634 B2 | 2/2016 | Brady et al. | |
| 9,265,635 B2 | 2/2016 | Walak | |
| 9,387,099 B2 | 7/2016 | McHugo | |
| 9,388,517 B2 | 7/2016 | Lilburn et al. | |
| 9,539,083 B2 | 1/2017 | Krimsky et al. | |
| 9,539,126 B2 | 1/2017 | Walsh et al. | |
| 9,687,367 B2 | 6/2017 | Gill et al. | |
| 9,895,242 B2 | 2/2018 | Sheldon et al. | |
| D834,193 S | 11/2018 | Erzberger | |
| 10,149,776 B2 | 12/2018 | Brady et al. | |
| 10,369,030 B2 | 8/2019 | Treacy et al. | |
| D867,595 S | 11/2019 | Armer et al. | |
| D883,485 S | 5/2020 | Carpenter et al. | |
| D887,003 S | 6/2020 | Garza et al. | |
| 2002/0042564 A1 | 4/2002 | Cooper et al. | |
| 2003/0040804 A1 | 2/2003 | Stack et al. | |
| 2003/0069647 A1 | 4/2003 | Desmond, III et al. | |
| 2003/0083734 A1 | 5/2003 | Friedrich et al. | |
| 2003/0164168 A1 | 9/2003 | Shaw | |
| 2004/0117031 A1 | 6/2004 | Stack et al. | |
| 2004/0148032 A1 | 7/2004 | Rutter et al. | |
| 2004/0215310 A1 | 10/2004 | Amirana | |
| 2005/0033310 A1* | 2/2005 | Alferness ......... A61B 17/12022 606/108 |
| 2005/0096733 A1 | 5/2005 | Kovneristy et al. | |
| 2005/0145253 A1 | 7/2005 | Wilson et al. | |
| 2005/0273160 A1 | 12/2005 | Lashinski et al. | |
| 2006/0130830 A1 | 6/2006 | Barry | |
| 2007/0055358 A1 | 3/2007 | Krolik et al. | |
| 2008/0072914 A1 | 3/2008 | Hendricksen et al. | |
| 2008/0221670 A1 | 9/2008 | Clerc et al. | |
| 2009/0157158 A1 | 6/2009 | Ondracek et al. | |
| 2009/0264991 A1 | 10/2009 | Paul, Jr. et al. | |
| 2009/0287299 A1 | 11/2009 | Tabor et al. | |
| 2010/0168839 A1 | 7/2010 | Braido et al. | |
| 2010/0234937 A1* | 9/2010 | Wang ............ A61B 17/12104 623/1.18 |
| 2011/0017207 A1 | 1/2011 | Hendricksen et al. | |
| 2011/0071613 A1 | 3/2011 | Wood et al. | |
| 2011/0079315 A1 | 4/2011 | Norton et al. | |
| 2011/0146673 A1* | 6/2011 | Keast ............ A61B 18/1477 128/200.24 |
| 2012/0046728 A1 | 2/2012 | Huser et al. | |
| 2012/0095483 A1 | 4/2012 | Babkes et al. | |
| 2012/0253471 A1 | 10/2012 | Tully et al. | |
| 2012/0259407 A1 | 10/2012 | Clerc et al. | |
| 2012/0296414 A1 | 11/2012 | Hartley | |
| 2013/0066415 A1 | 3/2013 | Hocking | |
| 2013/0103163 A1 | 4/2013 | Krimsky et al. | |
| 2013/0116775 A1 | 5/2013 | Roeder et al. | |
| 2013/0144372 A1 | 6/2013 | Wood et al. | |
| 2014/0058433 A1 | 2/2014 | Barrett et al. | |
| 2014/0074220 A1 | 3/2014 | Clerc et al. | |
| 2014/0082924 A1 | 3/2014 | Lundkvist et al. | |
| 2014/0180393 A1 | 6/2014 | Roeder | |
| 2014/0288588 A1 | 9/2014 | Lam et al. | |
| 2015/0051709 A1 | 2/2015 | Vasquez et al. | |
| 2015/0209136 A1 | 7/2015 | Braido et al. | |
| 2015/0265438 A1 | 9/2015 | Hossainy et al. | |
| 2016/0081787 A1 | 3/2016 | Parodi et al. | |
| 2016/0158037 A1 | 6/2016 | Shin et al. | |
| 2016/0338822 A1 | 11/2016 | Rocha | |
| 2017/0135835 A1 | 5/2017 | Matsunami et al. | |
| 2017/0172771 A1 | 6/2017 | Bruckheimer et al. | |
| 2017/0304093 A1 | 10/2017 | During et al. | |
| 2017/0333230 A1 | 11/2017 | Folan et al. | |
| 2018/0021154 A1 | 1/2018 | Leanne et al. | |
| 2018/0055631 A1 | 3/2018 | Morin et al. | |
| 2018/0092731 A1 | 4/2018 | Radhakrishnan et al. | |
| 2018/0104043 A1 | 4/2018 | Schlick et al. | |
| 2018/0125630 A1 | 5/2018 | Hynes et al. | |
| 2018/0153676 A1 | 6/2018 | Gong et al. | |
| 2018/0214141 A1 | 8/2018 | Mendez | |
| 2018/0289486 A1 | 10/2018 | Moll et al. | |
| 2019/0175374 A1 | 6/2019 | Park et al. | |
| 2019/0254817 A1 | 8/2019 | Centola et al. | |

FOREIGN PATENT DOCUMENTS

| | | | | |
|---|---|---|---|---|
| WO | 03020338 A2 | 3/2003 | | |
| WO | 2004010845 A2 | 2/2004 | | |
| WO | WO-2005013835 A1 * | 2/2005 | ....... A61B 17/12136 |
| WO | WO-2012042287 A1 * | 4/2012 | ............... A61F 2/04 |
| WO | 2016200103 A1 | 12/2016 | | |
| WO | 2018027145 A1 | 2/2018 | | |

OTHER PUBLICATIONS

European Patent Office Communication Pursuant to Article 94(3) EPC for European Patent Application No. 16169972.3 dated Oct. 29, 2019, 6 pages.

Hagl et al. "External Stabilization of Long-Segment Tracheobronchomalacia Guided by Intraoperative Bronchoscopy." The Annals of Thoracic Surgery, vol. 64, No. 5, 1997, pp. 1412-1421.

Xavier et al. "Development of a Modified Dumon Stent for Tracheal Applications: an Experimental Study in Dogs." J. Bras. Pneumol. 2008; 34(1): 21-26.

* cited by examiner

IMPLANTABLE ARTIFICIAL BRONCHUS AND USE OF AN IMPLANTABLE ARTIFICIAL BRONCHUS

CROSS-REFERENCE TO RELATED APPLICATIONS

This application is a continuation of U.S. patent application Ser. No. 15/156,841, filed on May 17, 2016 entitled "Implantable Artificial Bronchus and Use of an Implantable Artificial Bronchus" which claims priority to Brazilian Patent Application No. 10 2015 011376 5 filed May 18, 2015, each of which is incorporated by reference herein in its entirety.

FIELD OF THE INVENTION

The instant patent of invention relates to artificial bronchi for the treatment of pulmonary emphysema, and may be associated with a one-way valve.

BACKGROUND OF THE INVENTION

Pulmonary emphysema is a type of chronic obstructive pulmonary disease (COPD), which is characterized by the permanent enlargement of the gas exchange units (acini) associated with the destruction of alveolar walls, without fibrosis.

The destruction of these alveolar walls shows distinct patterns in each person, with different distribution and intensity. This gradual and irreversible rupture of lung tissue leads to the loss of the elastic capacity of lung recoil, namely, the loss of the ability to expel inspired air. As a result, there is a structural derangement of the rib cage, increase of the thorax diameters and diaphragm rectification (air entrapment and hyperinflation).

Areas affected by the disease fill the thoracic cavity, leaving less volume available for the healthy areas of lung tissue perform hematosis. The loss of respiratory capacity leads to a progressive functional disability of individuals with the disease.

Although there is no cure for pulmonary emphysema, there are some forms of treatment, including medicines, muscle training and oxygen therapy. For some more severe cases, a lung volume reduction surgery or lung transplantation may be indicated. While the medicines and muscle training have limited results, the lung volume reduction surgery and lung transplantation are very traumatic, and a very limited number of patients can be submitted to these treatments.

Since the year 2000, several less traumatic alternatives have been proposed to alleviate the suffering of patients with pulmonary emphysema.

a) Methods based on forced scarring of the sick tissue using chemicals or steam to produce mechanical retraction. These techniques are still being assessed and have the risk of producing or accelerating the damage caused by the disease itself after an initial improvement.

b) The European patent EP1524942 describes a self-expanding nitinol endobronchial valve covered by a silicone membrane, which has a structure that allows unidirectional air flow. This valve is implanted in areas close to the affected regions, causing the air accumulated therein to be expelled. Due to its unidirectional characteristic, it does not allow the reentry of air into the affected areas. The problem of this technique is the collateral communication between the entrapped air in the treated area and the remaining parts of the same lung. Another problem is that the working tissue should be excluded, for there to be a beneficial effect.

c) An alternative approach was the creation of ancillary air passages in the bronchi wall, to allow lung emptying. Although this alternative presents a more efficient solution over the affected lung, the existing state of the art results demonstrated the premature closure of these passages.

d) There is also treatment with mechanical retraction of the airways, where nitinol spirals (nickel-titanium alloy) are implanted using a straightened bronchoscope and, after the implant, the covers that keep the spiral straightened are removed, causing it to return to its original conformation, thus performing the retraction of the pulmonary parenchyma. This method is limited due to its irreversibility, inability of using an anticoagulant medication (for circulatory illnesses), a very high risk in patients with high pulmonary arterial pressure and lack of effect on patients affected with an advanced form of the disease, when there is not almost lung parenchyma.

Thus, there is the need for an alternative, a procedure that is not aggressive to the lung and that promotes lung disinsufflation without excluding its healthy areas.

DESCRIPTION OF THE INVENTION

Figure 1:
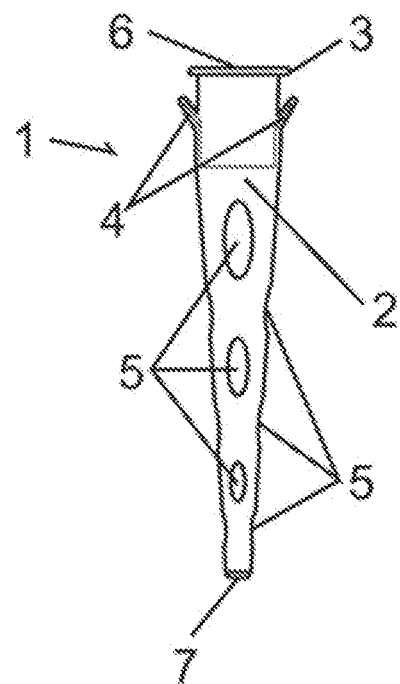
FIGS. 1 and 2 respectively represent the front and side views of an embodiment of the implantable artificial bronchus (1), according to this invention.
Figure 2:
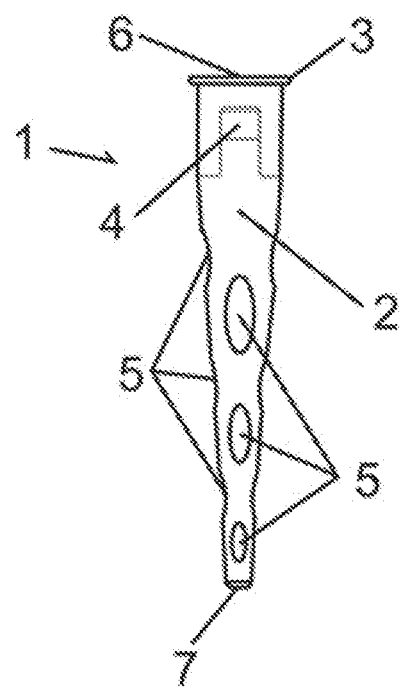
Figure 3:
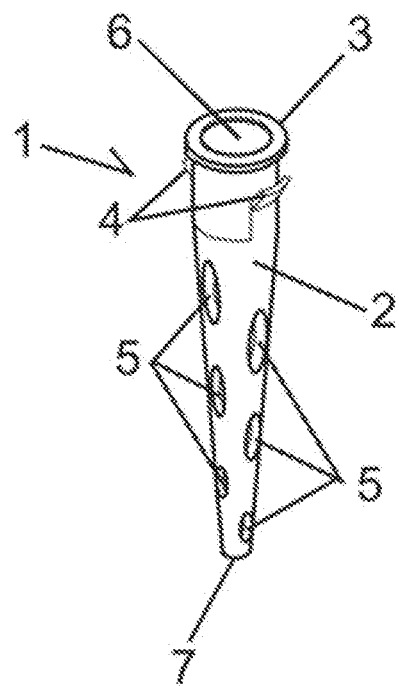
FIGS. 3 and 4 respectively represent upper and lower profile views of the implantable artificial bronchus (1).
Figure 4:
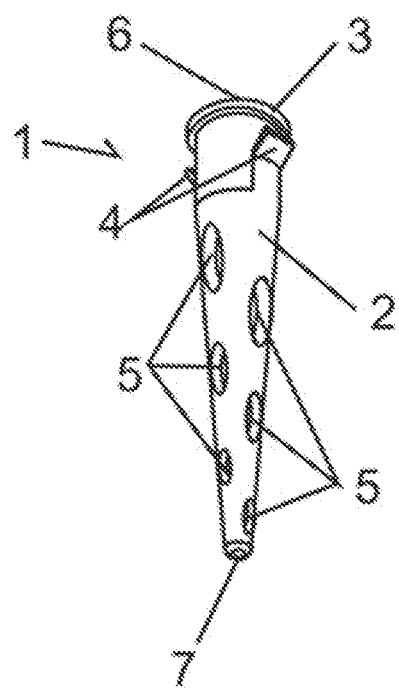
Figure 5:
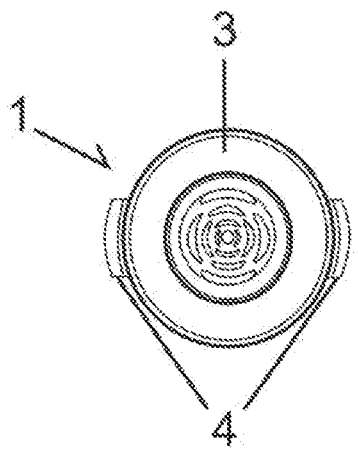
FIG. 5 shows the upper view of the implantable artificial bronchus (1).
Figure 6:
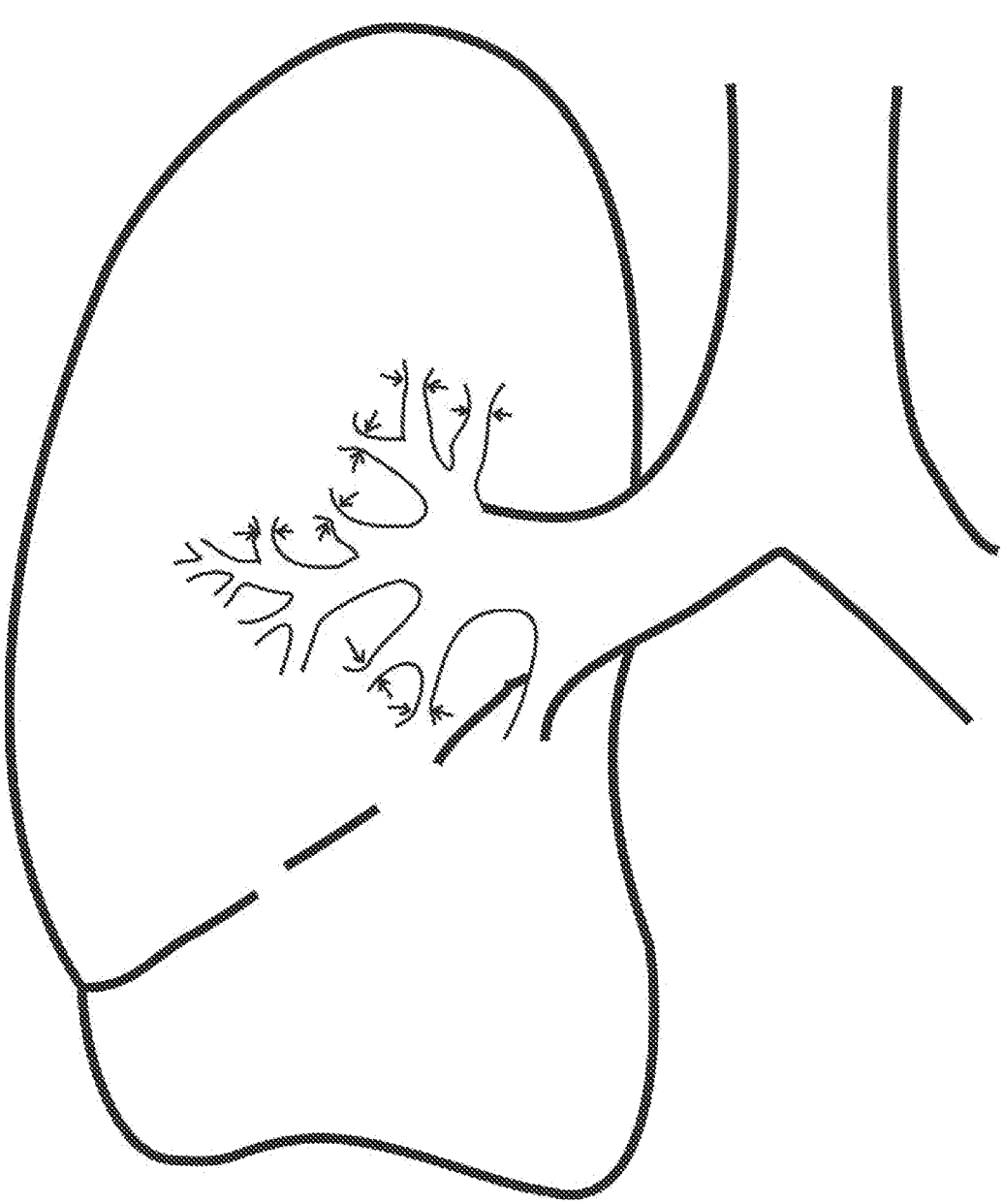
FIG. 6 represents a lung showing the branches of the airway. The arrows represent compression that the air exerted on the same.
Figure 7:
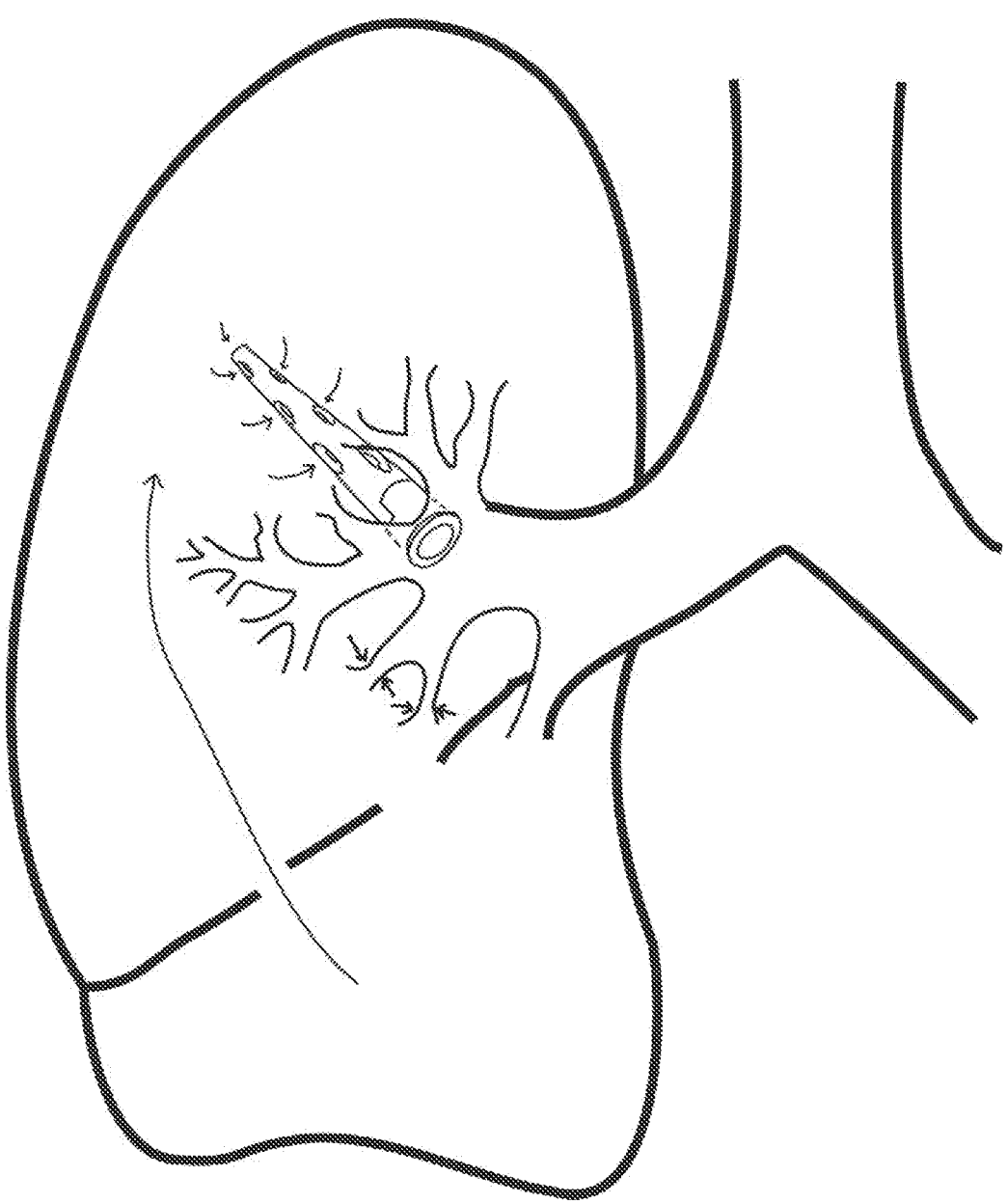
FIG. 7 shows the use of an implanted embodiment of implantable artificial bronchus, according to the present invention.
Figure 8:
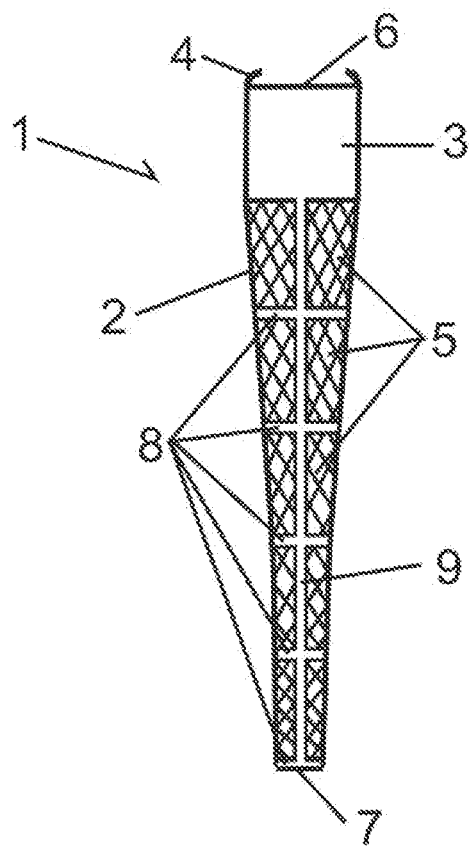
FIG. 8 represents another embodiment of the implantable artificial bronchus, made with a nitinol web.
Figure 9:
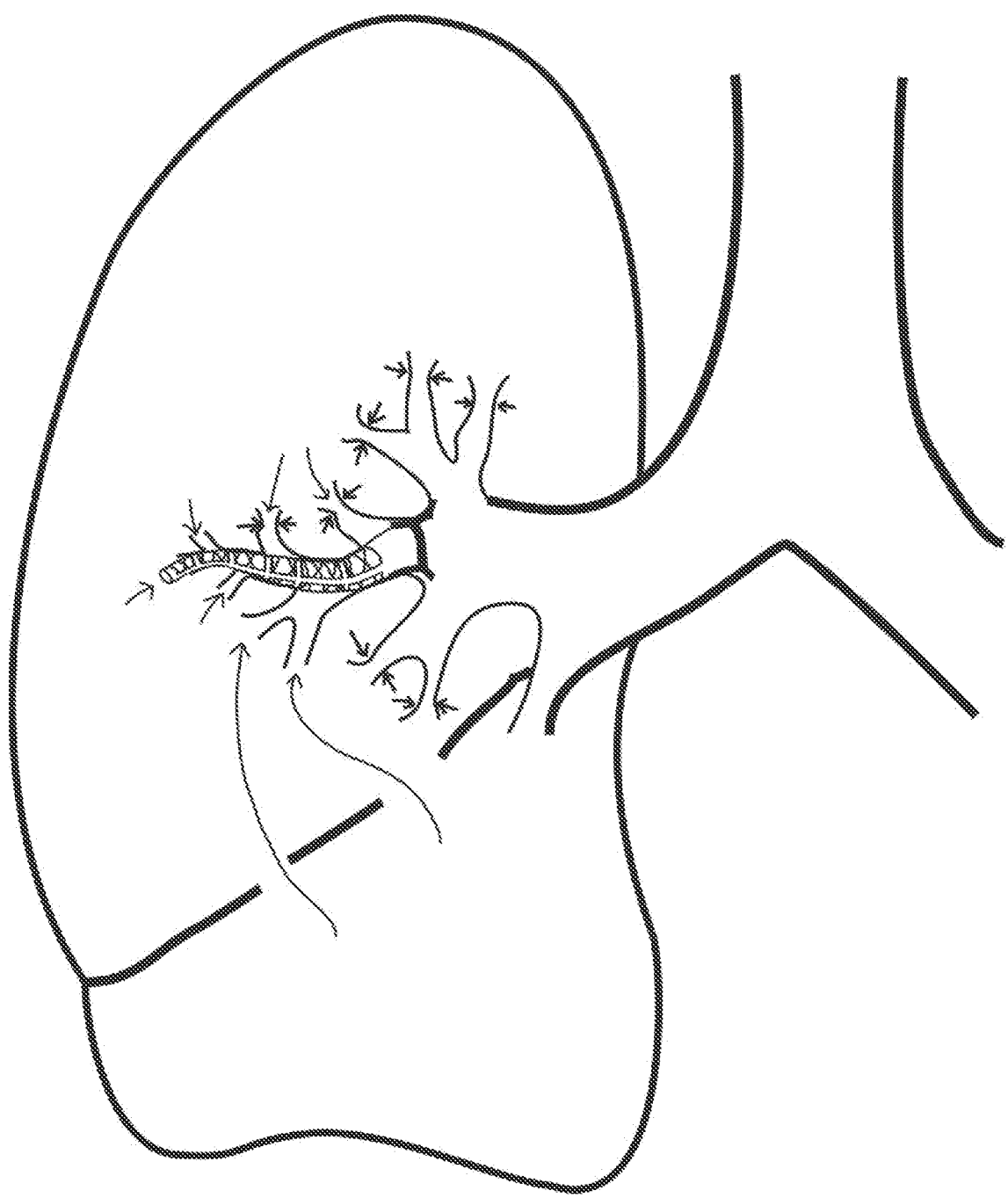
FIG. 9 represents the use of another embodiment of the implantable artificial bronchus.

In order to meet the need for an effective form of treatment, which is not an aggressive or an invasive procedure for the body, an implantable artificial bronchus (IAB) was developed.

The IAB, according to the present invention, consists of a tapered cylindrical body, where the upper nozzle is greater than the lower opening, comprising openings along its length and side wings.

In this invention, openings are any kind of side perforation or leakage from a network assembly.

The IAB (1) can be built in two alternative forms, with a silicone body (SB) or a nitinol web body (NWB), wherein both comprise in the body (2) a nozzle (3) and side wings (4), with side openings (5), upper (6) and lower (7) which enable the peripheral range for promoting lung deflation, which may have various longitudinal lengths.

In the SB assembly, the side wings are used for fixing the same in the air way/lung parenchyma, and in the NWB assembly, they enable a better handling, in case of IAB withdrawal.

The NWB embodiment further has silicone or fluoropolymer like polytetrafluoroethylene rings (8) and longitudinal rods (9), of silicone or fluoropolymer like polytetrafluoroethylene, and these structures prevent the incorporation of the nitinol web by the lung wall, and also preserves the possibility of IAB withdrawal in case of rejection or need to reimplant.

Another embodiment of this invention is the association of IAB with a one-way valve, as described in EP1524942— of H. Michael to Emphasys Medical Inc., published on Apr. 27, 2005, incorporated herein by reference. This association prevents lung parenchyma against injuries caused by dry air and moisture reduction, thus avoiding tissue reaction and closure by healing of those openings.

The IAB (1) features a (proximal) upper opening (6) which allows the association with the one-way valve, and also its maintenance, since it allows the removal of the valve, device cleaning with bronchoscope and valve reimplantation. In some embodiments, a length of the implantable artificial bronchus is greater than 5 times a size of a largest diameter of the implantable artificial bronchus. In some embodiments, the diameter of the proximal upper opening is greater than twice the diameter of the distal lower opening. In some embodiments, the body is configured to curve in a first radial direction along a first length of the body and in a second radial direction opposite the first radial direction along a second length of the body.

The use of this device is made by bronchoscopy. Initially, it is necessary to identify the locations where it is desired to carry out the application, through an image study obtained by computed tomography of the thorax, associated or not to a three-dimensional reconstruction program.

After identifying the positions, the application can be performed in two ways, one for IAB with SB, which begins with the passage of the needle for piercing the bronchial wall and introducing the guide wire in the lung parenchyma, and optionally, the balloon dilator can be passed.

The implanting of IAB with NWB does not require perforations into the lung wall. The implant path is initially identified with a malleable metal guide. A subsequent catheter passage can be done to guide the compressed IAB or the compressed IAB can be introduced directly by guidewire. After withdrawing the catheter, the IAB naturally expands and remain on the airway, promoting the enlargement of this path and providing causing lung deflation.

The present invention avoids the state of the art problems, since its cylindrical body allows the implantation without the need for extensive cuts or openings that trigger healing processes, or along the airways. Moreover, in the second embodiment according to the present invention, there is no need for any perforation except eventually for very distal airway. Additionally, its conformation with decreasing radius along the body, with side openings, promotes swirling of the air which enters the IAB. Thus, there is no sudden entry and the air is dispersed more evenly, thus ensuring an efficient and safe distribution, without causing tissue healing.

The use of IAB provides more safety and effectiveness in the treatment of lung emphysema, since it allows the air exit, does not trigger the healing mechanisms and does not destroy or annul the normal lung tissue.

It shall be understood that the embodiments described above are merely illustrative and any modification to them may occur for a person skilled in the art. Therefore, the present invention should not be considered as being limited to the embodiments described in this document.

The person skilled in the art will be able to readily evaluate, by means of the teachings contained in the text and in the presented examples, advantages of the invention, and to propose modifications and equivalent alternatives to the embodiments, without departing from the scope of the invention, as defined in the attached claims.

The invention claimed is:

1. A method of promoting lung disinsufflation, the method comprising:
   inserting a catheter into a bronchial passage of a patient's lung, the catheter containing an implantable artificial bronchus having a sidewall and a plurality of side openings extending through the sidewall, the implantable artificial bronchus being compressed within the catheter;
   using the catheter to position the implantable artificial bronchus in the bronchial passage such that the sidewall of the implantable artificial bronchus extends across openings of a plurality of other bronchial passages; and
   withdrawing the catheter from the bronchial passage to cause the implantable artificial bronchus to naturally expand and remain in the bronchial passage, the implantable artificial bronchus configured to promote enlargement of the bronchial passage and allow air to exit from the plurality of other bronchial passages and into the implantable artificial bronchus through one or more of the plurality of side openings, wherein the implantable artificial bronchus includes:
      a proximal upper opening; a distal lower opening in fluid communication with the proximal upper opening;
      a nozzle being cylindrical in shape and extending distally from the proximal upper opening; and
      a body coupled to a distal end of the nozzle and extending between a distal end of the nozzle and the distal lower opening, the body tapering along a majority of the body from the distal end of the nozzle toward the distal lower opening, wherein a diameter of the proximal upper opening is larger than a diameter of the distal lower opening.

2. The method of claim 1, wherein a length of the implantable artificial bronchus is greater than 5 times a size of a largest diameter of the implantable artificial bronchus.

3. The method of claim 1, wherein the diameter of the proximal upper opening is greater than twice the diameter of the distal lower opening.

4. The method of claim 1 further comprising:
   performing a bronchoscopy to identify a location of the bronchial passage.

5. The method of claim 1 further comprising:
   identifying an implant path to the bronchial passage without perforating a lung wall.

6. The method of claim 5, wherein only a distal end of the bronchial passage is perforated during implanting the implantable artificial bronchus.

7. The method of claim 1 further comprising:
   identifying an implant path to the bronchial passage using a malleable metal guide.

8. The method of claim 1, wherein the nozzle does not include a valve.

9. The method of claim 1, wherein the nozzle includes a closed cylindrical sidewall.

10. The method of claim 1, wherein the implantable artificial bronchus includes a body being a web comprised of nitinol.

11. The method of claim 1, wherein the body tapers continuously from the nozzle to the distal lower opening.

12. The method of claim 1, wherein the implantable artificial bronchus includes a body configured to curve in a first radial direction along a first length of the body and in a second radial direction opposite the first radial direction along a second length of the body.

13. The method of claim 1 further comprising:
a plurality of side wings extending longitudinally and radially inwardly from a proximal upper opening of the implantable artificial bronchus toward one another.

14. The method of claim 1, wherein the implantable artificial bronchus includes a body having silicone rods and one of silicone rings or fluoropolymer rings.

15. The method of claim 1, wherein the plurality of other bronchial passages includes three or more other bronchial passages.

16. The method of claim 1, wherein the plurality of other bronchial passages includes four or more other bronchial passages.

17. The method of claim 1, wherein the body tapers from the distal end of the nozzle to a portion proximate the distal lower opening.

18. The method of claim 1, wherein the body tapers from the distal end of the nozzle to a distal end of the distal lower opening.

19. The method of claim 1, wherein the body includes a length extending from the distal end of the nozzle to the distal lower opening and the body tapers at a generally constant rate along a length of the body.

20. A method of promoting lung disinsufflation, the method comprising:
inserting a catheter into a bronchial passage of a patient's lung, the catheter containing an implantable artificial bronchus having a plurality of side openings and compressed within the catheter;
using the catheter to position the implantable artificial bronchus in the bronchial passage such that the implantable artificial bronchus extends across openings of a plurality of other bronchial passages; and
withdrawing the catheter from the bronchial passage to cause the implantable artificial bronchus to naturally expand and remain in the bronchial passage, the implantable artificial bronchus configured to promote enlargement of the bronchial passage and allow air to exit from the plurality of other bronchial passages and into the implantable artificial bronchus through one or more of the plurality of side openings,
wherein the implantable artificial bronchus includes:
a proximal upper opening;
a distal lower opening in fluid communication with the proximal upper opening, wherein a diameter of the proximal upper opening is larger than a diameter of the distal lower opening;
a nozzle being cylindrical in shape and extending distally from the proximal upper opening, wherein a length of the nozzle is generally equal in size to a diameter of the nozzle; and
a body coupled to a distal end of the nozzle and extending between a distal end of the nozzle and the distal lower opening, the body tapering along a majority of the body from the distal end of the nozzle toward the distal lower opening and the plurality of side openings configured to allow air to enter into and exit the implantable artificial bronchus through the body.

* * * * *